US012369782B2

(12) United States Patent
Akui

(10) Patent No.: US 12,369,782 B2
(45) Date of Patent: Jul. 29, 2025

(54) ENDOSCOPE HAVING OPERATION PORTION WITH SURFACE FOR RESTRICTING MOVEMENT OF TUBE AND SEAL

(71) Applicant: OLYMPUS CORPORATION, Tokyo (JP)

(72) Inventor: Nobuaki Akui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 412 days.

(21) Appl. No.: 17/901,013

(22) Filed: Sep. 1, 2022

(65) Prior Publication Data

US 2022/0409028 A1 Dec. 29, 2022

Related U.S. Application Data

(63) Continuation of application No. PCT/JP2020/009486, filed on Mar. 5, 2020.

(51) Int. Cl.
*A61B 1/012* (2006.01)
*A61B 1/00* (2006.01)
*A61B 1/005* (2006.01)

(52) U.S. Cl.
CPC .......... *A61B 1/012* (2013.01); *A61B 1/00119* (2013.01); *A61B 1/0055* (2013.01); *A61B 1/0057* (2013.01); *A61B 1/00066* (2013.01)

(58) Field of Classification Search
USPC ................................. 600/130, 131, 153, 154
See application file for complete search history.

(56) References Cited

U.S. PATENT DOCUMENTS 4,552,129 A * 11/1985 Utsugi ................. A61B 1/0052
600/154
4,750,477 A * 6/1988 Wardle ................... A61B 1/307
600/149

(Continued)

FOREIGN PATENT DOCUMENTS

JP S57-185301 A 11/1982
JP S63-54143 A 3/1988

(Continued)

OTHER PUBLICATIONS

Machine language translation of JPS57-185301, Nov. 1982 (Year: 1982).*

(Continued)

*Primary Examiner* — John P Leubecker
(74) *Attorney, Agent, or Firm* — Scully, Scott, Murphy & Presser, P.C.

(57) ABSTRACT

An endoscope includes an operation portion provided on a proximal end side of an insertion portion and a treatment instrument insertion port to which a treatment instrument is inserted, and includes a forceps pipe sleeve provided in the operation portion with an axis direction of a central axis passing through the treatment instrument insertion port being different from an axis direction of the insertion portion, a flexible channel tube extending in a bent state from a proximal end of the insertion portion toward a forceps pipe sleeve and connected to the forceps pipe sleeve by insertion inside the operation portion, and a guide wall provided inside the operation portion and being contactable with an outer side portion of a bend of the channel tube by abutting on the channel tube.

20 Claims, 9 Drawing Sheets

(56) References Cited

U.S. PATENT DOCUMENTS

| | | | | |
|---|---|---|---|---|
| 4,765,312 A | * | 8/1988 | Sasa | A61B 1/00128 600/153 |
| 4,771,766 A | * | 9/1988 | Aoshiro | A61B 1/121 600/155 |
| 4,791,912 A | * | 12/1988 | Tashiro | A61B 1/00137 600/153 |
| 4,874,364 A | * | 10/1989 | Morris | A61B 1/00137 604/35 |
| 4,967,732 A | * | 11/1990 | Inoue | A61B 1/00137 600/149 |
| 5,902,315 A | * | 5/1999 | DuBois | A61B 17/00234 600/210 |
| 2004/0167379 A1 | * | 8/2004 | Akiba | A61B 1/018 600/154 |
| 2007/0088199 A1 | * | 4/2007 | Ito | A61B 1/00137 600/156 |
| 2012/0253127 A1 | * | 10/2012 | Yamane | A61B 1/00137 600/154 |
| 2015/0265139 A1 | | 9/2015 | Shintani | |

FOREIGN PATENT DOCUMENTS

| | | |
|---|---|---|
| JP | S63-184005 A | 7/1988 |
| JP | 2004-248777 A | 9/2004 |
| JP | 5711433 B1 | 4/2015 |
| WO | 2014/185186 A1 | 11/2014 |
| WO | 2021/260790 A1 | 12/2021 |

OTHER PUBLICATIONS

International Search Report dated Jun. 9, 2020 received in PCT/JP2020/009486.

* cited by examiner

ENDOSCOPE HAVING OPERATION PORTION WITH SURFACE FOR RESTRICTING MOVEMENT OF TUBE AND SEAL

CROSS REFERENCE TO RELATED APPLICATION

This application is a continuation application of PCT/JP2020/009486 filed on Mar. 5, 2020, the entire contents of which are incorporated herein by this reference.

BACKGROUND OF THE INVENTION

1. Field of the Invention

The present invention relates to an endoscope having a channel tube through which a treatment instrument is inserted and through which air or water is fed.

2. Description of the Related Art

Conventionally, endoscopes are widely used in a medical field. By inserting an elongated insertion portion of an endoscope into a body cavity of a subject, an organ inside the body cavity may be observed. Further, the endoscope includes a channel tube inserted into the insertion portion, and various treatments can be performed using treatment instruments inserted into the channel tube, and air feeding, water feeding, and the like can be performed through the channel tube.

A proximal end side of such a channel tube is connected to a tubular member such as a forceps pipe sleeve provided in an operation portion. In this case, in general, since an axis direction of a central axis of the forceps pipe sleeve or the like is different from an axis direction of a central axis of the insertion portion of the endoscope, the channel tube is disposed in a bent state inside the operation portion.

Therefore, when the treatment instrument or the like is inserted from the forceps pipe sleeve or the like, a predetermined pressing force may act on an inner wall of a bending portion of the channel tube. In order to prevent the channel tube from falling off from the forceps pipe sleeve or the like due to such a pressing force, the channel tube is generally connected to the forceps pipe sleeve or the like by adhesion or the like.

Further, for example, Japanese Patent No. 5711433 discloses a configuration in which a proximal end portion of a tube is sandwiched between a tubular member (pipe sleeve portion) provided in a first main body portion and a second main body portion externally mounted on the tubular member, and an O-ring is interposed between the tube and the tubular member, thereby firmly connecting the tube to the tubular member while securing watertightness and airtightness.

SUMMARY OF THE INVENTION

An endoscope according to an aspect of the present invention includes an operation portion provided on a proximal end side of an insertion portion to be inserted into a subject, a tubular member provided in the operation portion and having an opening portion into which a treatment instrument is inserted, a channel tube extending from the insertion portion to the inside of the operation portion and inserted into the tubular member to be connected to the tubular member, and a sealing member disposed between a distal end side of the tubular member and the channel tube, the channel tube is restricted from falling off from the tubular member by a restoring force of the compressed sealing member.

DETAILED DESCRIPTION OF THE PREFERRED EMBODIMENT(S)

Hereinafter, an embodiment of the present invention will be described with reference to the accompanying drawings. The drawings relate to an embodiment of the present invention and FIG. 1 is a side view illustrating an endoscope.

Figure 1:
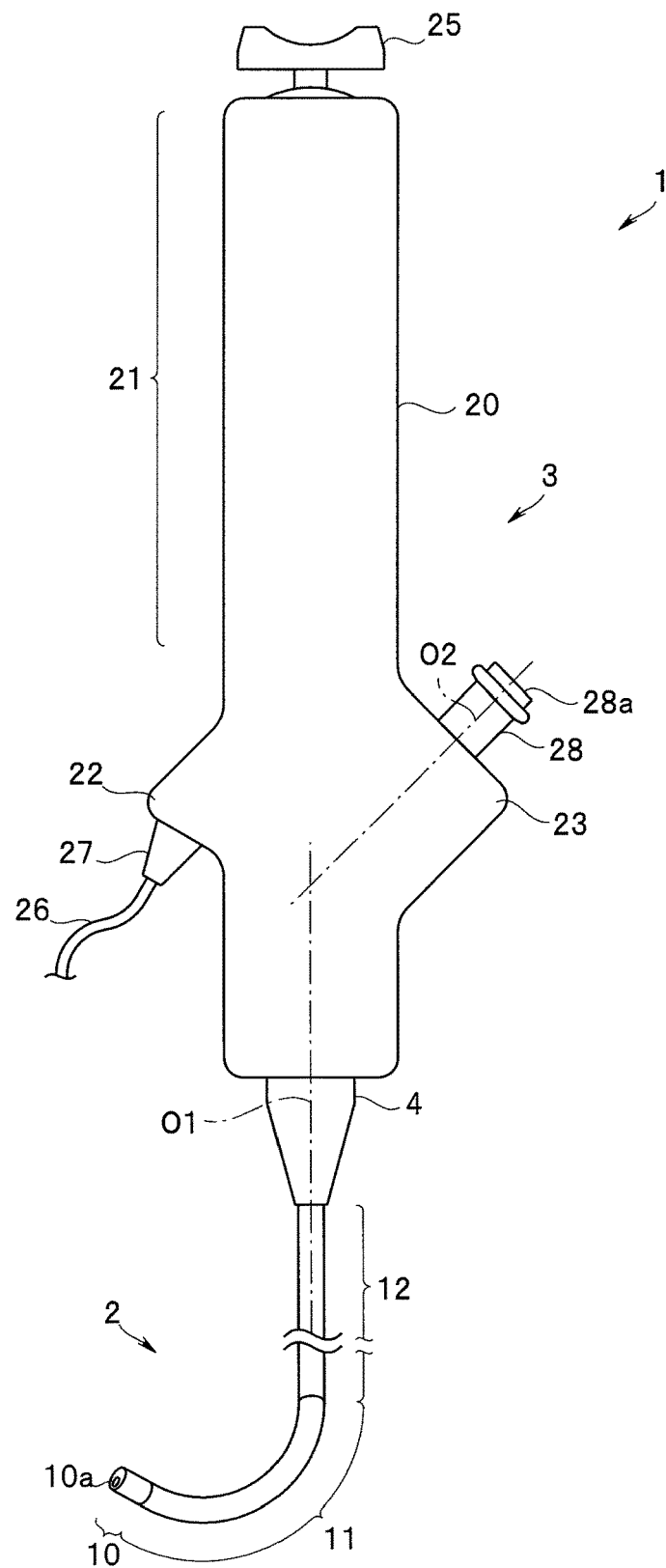
FIG. 1 is a left side view illustrating an endoscope.

An endoscope 1 illustrated in FIG. 1 is, for example, an endoscope suitable for observation and treatment of the renal pelvis, the ureter, and the like, and is a disposable endoscope which is not premised on reuse in the present embodiment. A main portion of the endoscope 1 is configured by including an elongated insertion portion 2 to be inserted into a subject, and an operation portion 3 consecutively connected to a proximal end side of a longitudinal axis (central axis) O1 of the insertion portion 2 with a bend preventing portion 4 interposed therebetween.

A main portion of the insertion portion 2 is configured with a distal end portion 10, a bending portion 11, and a flexible tube portion 12, in this order from the distal end side in a direction along the longitudinal axis O1.

Inside the distal end portion 10, for example, an image pickup unit connected to a signal line, an illumination optical system that irradiates a subject with illumination light transmitted by a light guide bundle (none are illustrated), and the like are provided.

Further, the distal end portion 10 is provided with a channel opening portion 10a connected to a distal end of a channel tube 15 (see FIGS. 2 and 3) which will be described later.

The bending portion 11 is configured to be bendable in, for example, four directions of up and down, and left and right in accordance with an operation of a bending operation lever 25 (to be described later) provided in the operation portion 3.

The flexible tube portion 12 is configured with a tubular member having flexibility.

The operation portion 3 includes, for example, a housing 20 having substantially a rectangular parallelepiped shape elongated in the longitudinal axis O1 direction of the insertion portion 2, and a region from the intermediate portion to the proximal end side of the operation portion 3 is set as a grasping portion 21 for a user or the like to grasp the operation portion 3.

The bending operation lever 25 is provided on the proximal end of the operation portion 3. In the present embodiment, the bending operation lever 25 is, for example, a joystick-type operation lever, and is configured to be tiltable in all directions including front and rear directions and left and right directions when viewed from the user who grasps the grasping portion 21 so that the distal end side (insertion portion 2 side) faces downward. The user or the like is able to perform a tilting operation of the bending operation lever 25 with, for example, the thumb of the hand grasping the grasping portion 21. In order to perform a bending operation of the bending portion 11 in conjunction with the tilting of the bending operation lever 25, for example, four bending operation wires (not illustrated) extending from the insertion portion 2 to the inside of the operation portion 3 are connected to the bending operation lever 25. However, since these configurations are well known, the description thereof will be omitted.

A front side protruding portion 22 having substantially a triangular shape in a side view is provided on the front side of the operation portion 3 on the distal end side with respect to the grasping portion 21. A universal cable 26 through which a signal line from the insertion portion 2, a light guide bundle, and the like are inserted extends from a lower surface of the front side protruding portion 22. More specifically, a bend preventing portion 27 is retained on a lower surface side of the front side protruding portion 22, and the universal cable 26 extends obliquely downward through the bend preventing portion 27.

Further, a rear side protruding portion 23 having substantially a triangular shape in a side view is provided on the rear surface side of the operation portion 3 on the distal end side with respect to the grasping portion 21. A forceps pipe sleeve 28 as a tubular member protrudes from an upper surface of the rear side protruding portion 23. In other words, the forceps pipe sleeve 28 of the present embodiment protrudes obliquely upward from the upper surface of the rear side protruding portion 23 in order to ensure good insertion property when a user or the like inserts the treatment instrument with the hand opposite to the hand grasping the grasping portion 21. Therefore, the forceps pipe sleeve 28 of the present embodiment is set such that the central axis O2 passing through a treatment instrument insertion port 28a, which is an opening portion, is different from the axis direction of the central axis O1 of the insertion portion 2 (that is, so that the central axis O2 intersects with the central axis O1 inside the operation portion 3).

Inside the operation portion 3, the channel tube 15 extending from the insertion portion 2 is connected to the forceps pipe sleeve 28. Here, the channel tube 15 is configured of a material having good sliding property such as polytetrafluoroethylene in order to improve insertion property of the treatment instrument or the like.

Next, a configuration of the distal end side of the operation portion 3 will be described with reference to FIGS. 2 and 3.

Figure 3:
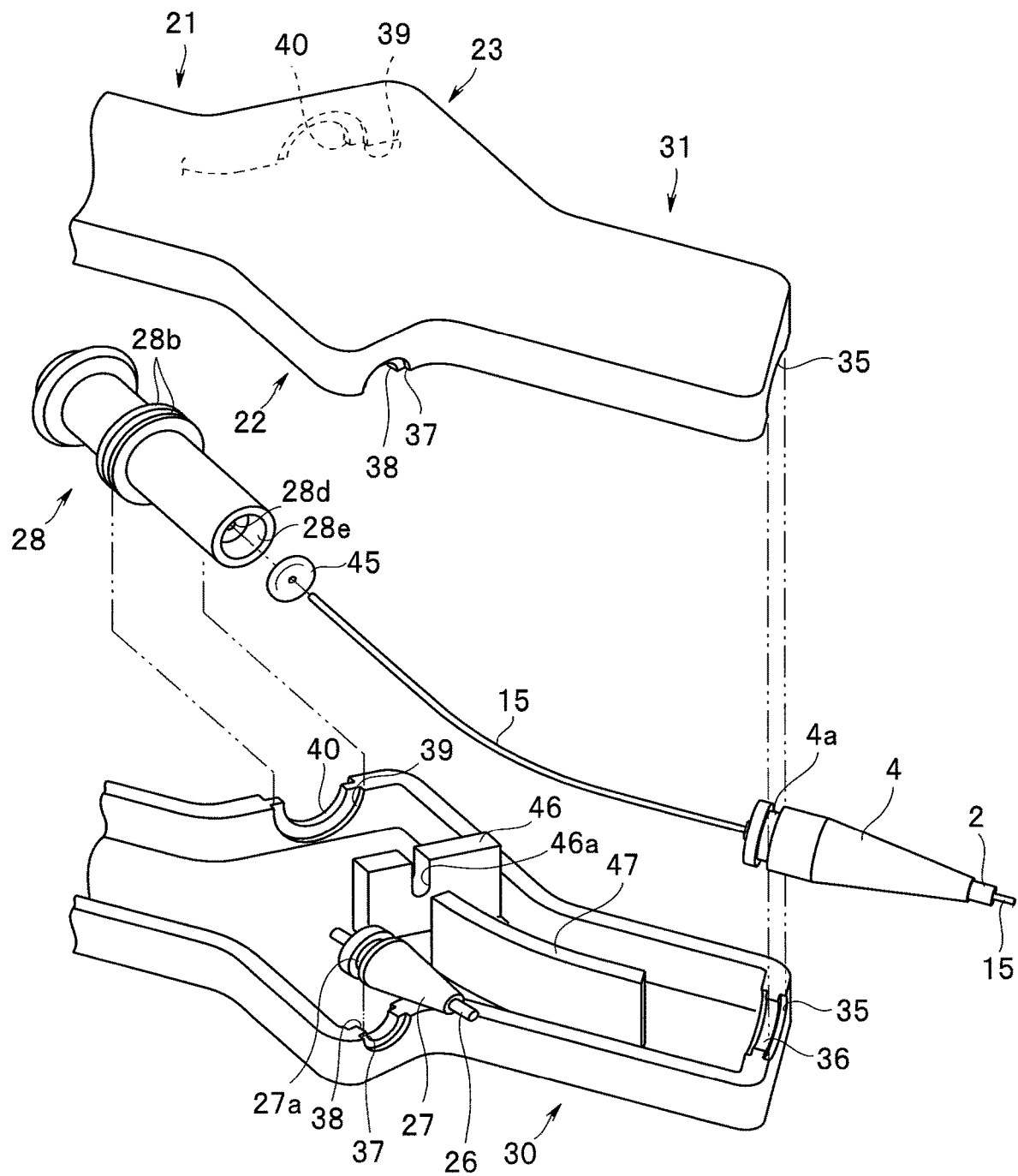
FIG. 3 is an exploded perspective view illustrating the main portion of the operation portion.

As illustrated in FIG. 3, the housing 20 configuring the operation portion 3 of the present embodiment is divided into and formed by left and right portions with a first housing member 30 mainly configuring a right side portion and a second housing member 31 mainly configuring a left side portion.

Wall portions forming the distal end surfaces of the first housing member 30 and the second housing member 31 are each provided with a semicircular cutout portion 35 having substantially the same diameter as the proximal end side of the bend preventing portion 4. Further, each of the cutout portions 35 is provided with a key 36 having a semicircular shape protruding in an inner diameter direction.

Each of the cutout portions 35 and each of the keys 36 form a stepped through-hole having a circular shape as a whole when the first housing member 30 and the second housing member 31 are joined to each other and retain the proximal end side of the insertion portion 2 to the operation portion 3 with the bend preventing portion 4 interposed therebetween.

In order to realize such retention, a key groove 4a to be fitted to each key 36 is provided on the proximal end side of the bend preventing portion 4.

When the first housing member 30 and the second housing member 31 are joined to each other, the proximal end portion of the bend preventing portion 4 is retained between each of the cutout portions 35, and each of the keys 36 is fitted into the key groove 4a. Thus, the bend preventing portion 4 retaining the proximal end side of the insertion portion 2 is fixed in a state of being positioned at a predetermined position with respect to the housing 20. The proximal end side of the insertion portion 2 is consecutively connected to the operation portion 3 through such fixation of the bend preventing portion 4.

In addition, in each of the first housing member 30 and the second housing member 31, a cutout portion 37 having a semicircular shape having substantially the same diameter as the proximal end side of the bend preventing portion 27 is provided in a wall portion forming the lower surface of the front side protruding portion 22. Further, each of the cutout portions 37 is provided with a key 38 having a semicircular shape protruding in an inner diameter direction.

When the first housing member 30 and the second housing member 31 are joined to each other, each of the cutout portions 37 and each of the keys 38 form a stepped through-hole having a circular shape as a whole and retain the proximal end side of the universal cable 26 with the bend preventing portion 27 interposed therebetween.

In order to realize such retention, a key groove 27a to be fitted to each key 38 is provided on the proximal end side of the bend preventing portion 27.

When the first housing member 30 and the second housing member 31 are joined to each other, the proximal end portion of the bend preventing portion 27 is retained between each of the cutout portions 37, and each key 38 is fitted into the key groove 27a. Thus, the bend preventing portion 27 retaining the proximal end side of the universal cable 26 is fixed in a state of being positioned at a predetermined position with respect to the housing 20. In other words, the proximal end side of the universal cable 26 is consecutively connected to the operation portion 3 through such fixation of the bend preventing portion 27.

In addition, in each of the first housing member 30 and the second housing member 31, a cutout portion 39 having a semicircular shape with a diameter larger than an outer diameter of the forceps pipe sleeve 28 is provided in a wall portion forming the upper surface of the rear side protruding portion 23. Further, each of the cutout portions 39 is provided with a key 40 having a semicircular shape protruding in an inner diameter direction.

Each of the cutout portions 39 and each of the keys 40 form a stepped through-hole having a circular shape as a whole when the first housing member 30 and the second housing member 31 are joined to each other and retain an intermediate portion of the forceps pipe sleeve 28 in the operation portion 3.

In order to realize such retention, a pair of outward flanges 28b having substantially the same diameters as the cutout portions 39 are provided in the intermediate portion of the forceps pipe sleeve 28 at substantially the same intervals as the width of the key 40.

When the first housing member 30 and the second housing member 31 are joined to each other, each outward flange 28b is retained by sandwiching each key 40 between each cutout portion 39. Accordingly, the forceps pipe sleeve 28 is fixed in a state of being positioned at a predetermined position with respect to the operation portion 3 such that the proximal end side protrudes to the outside of the housing 20 and the distal end side is disposed inside the housing 20.

Figure 2:
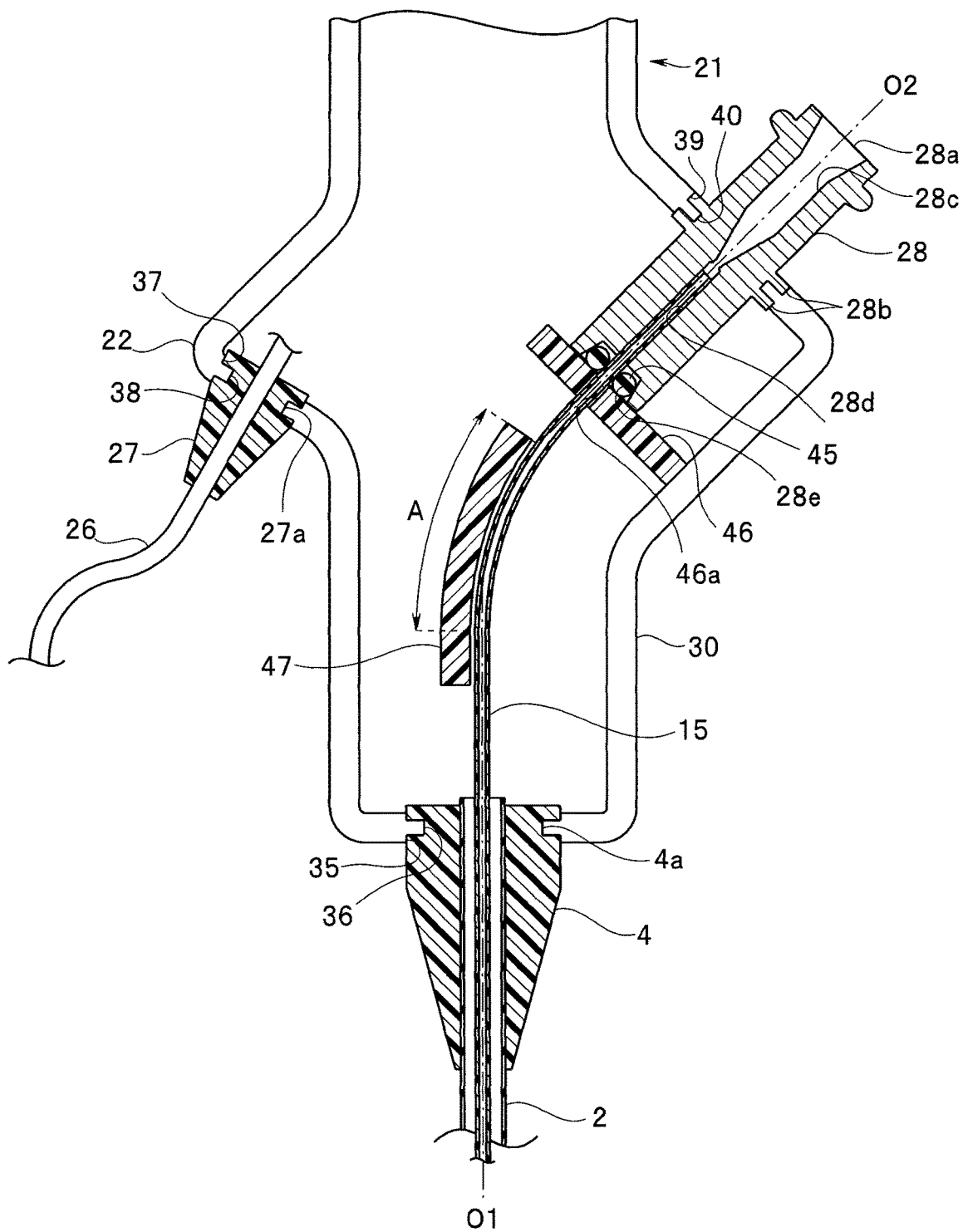
FIG. 2 is a cross-sectional view illustrating a main portion of an operation portion.

Here, as illustrated in FIG. 2, a tapered hole 28c is provided inside the forceps pipe sleeve 28. The tapered hole 28c is tapered from the treatment instrument insertion port 28a as a proximal end toward the intermediate portion of the distal end side. Inside the forceps pipe sleeve 28, the distal end of the tapered hole 28c communicates with a proximal end of a tube insertion hole 28d having substantially the same diameter as the channel tube 15. Further, inside the forceps pipe sleeve 28, a proximal end of a seal retention hole 28e having a larger diameter than the tube insertion hole 28d communicates with the distal end of the tube insertion hole 28d. The tapered hole 28c, the tube insertion hole 28d, and the seal retention hole 28e form a continuous through-hole penetrating from the proximal end side to the distal end side of the forceps pipe sleeve 28.

Inside the operation portion 3 (housing 20), the channel tube 15 extending from the proximal end of the insertion portion 2 is inserted and connected to the tube insertion hole 28d of the forceps pipe sleeve 28. Further, in order to secure airtightness and liquid-tightness between the forceps pipe sleeve 28 and the channel tube 15, an O-ring 45 as a sealing member is retained in the seal retention hole 28e in a state in which the channel tube 15 is penetrated.

Specifically, the proximal end side of the channel tube 15 inserted into the insertion portion 2 is extended without any change inside the operation portion 3 without being connected to a channel tube for relay or the like.

The channel tube 15 is disposed inside the operation portion 3 in a bent state from the axis direction of the central axis O1 of the insertion portion 2 toward the axis direction of the central axis O2 of the forceps pipe sleeve 28. The proximal end side of the channel tube 15 is inserted into the tube insertion hole 28d in an unadhered state after passing through the O-ring 45.

In general, since a material such as polytetrafluoroethylene is a material having low affinity with an adhesive, when the channel tube 15 configured of polytetrafluoroethylene or the like is adhered, a pretreatment such as an etching treatment (tetra-etching treatment) is necessary to be performed. However, since the channel tube 15 of the present embodiment is inserted into the tube insertion hole 28d in an unadhered state, the etching treatment or the like is not performed.

Here, inside the housing 20, a partition wall 46 as a regulation member is provided at a position close to and facing the distal end of the forceps pipe sleeve 28 retained by the housing 20 (see FIGS. 2 and 3).

The partition wall 46 is for preventing the O-ring 45 from falling off from the seal retention hole 28e. For this reason, the partition wall 46 is disposed at a position at which the interval between the partition wall 46 and the distal end of the forceps pipe sleeve 28 is less than the thickness of the O-ring 45 (more preferably, less than ½ of the thickness of the O-ring 45), and is integrally formed with the first housing member 30, for example. Further, the partition wall 46 is provided with substantially a U-shaped slit 46a, and the channel tube 15 is inserted into the tube insertion hole 28d via the slit 46a.

When the O-ring 45 has an outer diameter equal to or larger than the opening provided on the distal end side of the forceps pipe sleeve 28 and an inner diameter equal to or smaller than the outer diameter of the channel tube 15, watertightness can be secured without adhesion. In addition, the O-ring 45 is compressed and by a restoring force of the O-ring, the channel tube 15 is restricted from falling off.

Further, inside the operation portion 3, a guide wall 47 as an auxiliary member is provided at a position corresponding to at least a part of a bending region A of the channel tube 15 and at a position along an outer side portion of a bend of the channel tube 15.

When the treatment instrument or the like inserted from the treatment instrument insertion port 28a of the forceps pipe sleeve 28 passes through the bending region A in the channel tube 15, the guide wall 47 regulates the treatment instrument or the like from pressing against the inner walls of the channel tube 15 and moving toward the outer side direction of the bend. Therefore, the guide wall 47 has a wall surface having a bending shape from the axis direction of the central axis O1 of the insertion portion 2 toward the axis direction of the central axis O2 of the forceps pipe sleeve 28 (that is, a bending shape bent along the bending shape of the channel tube 15). Thus, the treatment instrument or the like is restricted to move toward the outer side direction of the bend and is guided to the insertion portion side of the endoscope along the bend of the wall surface of the guide wall 47. Here, the outer side direction of the bend refers to a direction toward the guide wall 47 when viewed from the bending region A in the channel tube 15 (that is, a direction toward the outside of the bend of the channel tube 15 from the bending region A in the channel tube 15).

The guide wall 47 is configured of a material more rigid than the channel tube 15 to ensure rigidity and is formed integrally with the first housing member 30, for example.

As described above, guide wall 47 is preferably configured of a material more rigid than the channel tube 15. However, for example, even when the material is the same, the rigidity may be ensured by changing (increasing) the thickness.

According to an embodiment with such a configuration, the proximal end side of the channel tube 15 may be connected to the forceps pipe sleeve 28 accurately with a simple configuration and simple work by including the forceps pipe sleeve 28 including the operation portion 3 provided on the proximal end side of the insertion portion 2 and the treatment instrument insertion port 28a for inserting the treatment instrument, and provided on the operation portion 3 such that the axis direction of the central axis O2 passing through the treatment instrument insertion port 28a is different from the axis direction of the insertion portion 2, the flexible channel tube 15 extending from the proximal end of the insertion portion 2 toward the forceps pipe sleeve 28 in a bent state inside the operation portion 3 and connected to the forceps pipe sleeve 28 by insertion, and the guide wall 47 provided in the operation portion 3 and contactable with the outer side portion of the bend of the channel tube 15 by abutting on the channel tube 15.

In other words, by adopting a configuration in which the channel tube 15 is connected to the forceps pipe sleeve 28 in an unadhered state by insertion, the channel tube 15 may be connected to the forceps pipe sleeve 28 without performing an etching process or the like, even when the channel tube 15 is configured with a material having low affinity with an adhesive such as polytetrafluoroethylene or the like. In this case, by providing the guide wall 47 inside the first housing member 30 and making it possible to contact with the outer side portion of the bend of the channel tube 15, even when a force pressing the channel tube 15 in the outer side direction of the bend is generated in the bending region A of the channel tube 15 when a treatment instrument or the like is inserted into the channel tube 15, the channel tube 15 can be more reliably prevented from falling off from the forceps pipe sleeve 28 compared to the case of only having the O-ring.

Figure 4:
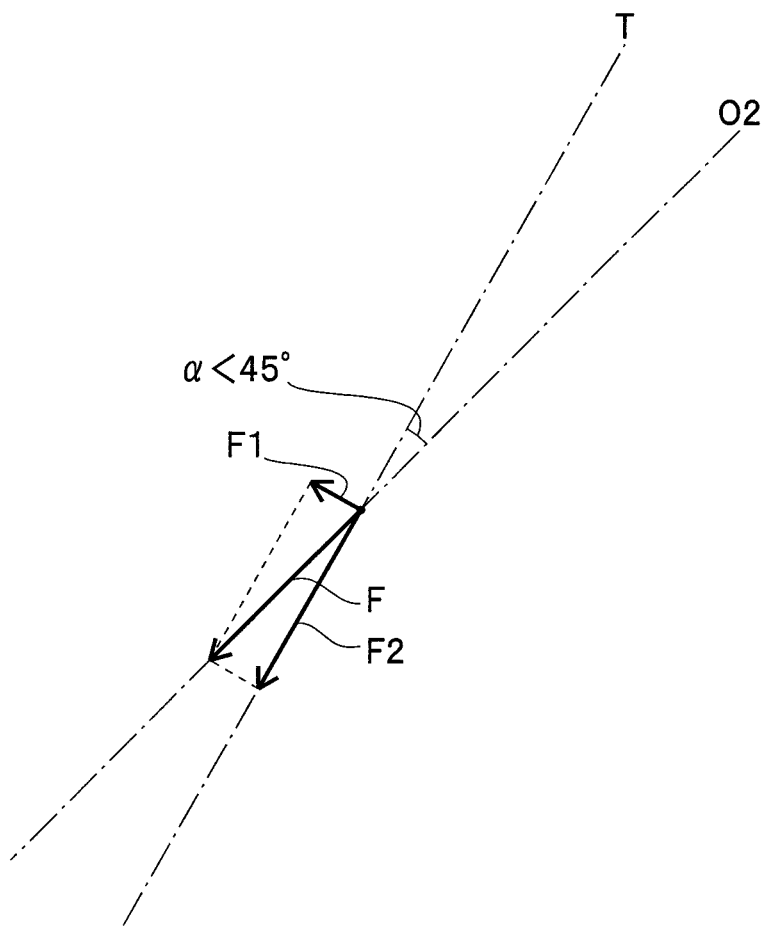
FIG. 4 is an explanatory view illustrating a component of a force for pressing a treatment instrument.

Further, as shown in FIGS. 2 and 4, by setting the angle α formed by the central axis O2 of the opening (treatment instrument insertion port 28a) of the forceps pipe sleeve 28 and a tangential line T to the guide wall 47 at the intersection position between the guide wall 47 and the central axis O2 of the opening of the forceps pipe sleeve 28 to 45 degrees or less, the force F of inserting treatment instrument or the like becomes larger in the force in the direction parallel to the guide wall 47 (in other words, the force F2 advancing in the channel tube 15) than the force in the direction perpendicular to the guide wall 47 (in other words, the force F1 pushing the guide wall 47) so that an amount of push toward the channel tube 15 can be reduced and prevention of falling off of the channel tube 15 can be further expected.

In addition, since the connection between the forceps pipe sleeve 28 and the channel tube 15 is configured to be of simple insertion without adhesion, strict management of the length of the channel tube 15 from the proximal end of the insertion portion 2 to the forceps pipe sleeve 28 is not necessary compared with a configuration in which the channel tube 15 is connected to the distal end side of the forceps pipe sleeve 28 by adhesion or the like. In other words, for example, when the insertion depth of the channel tube 15 with respect to the tube insertion hole 28d is slightly shallow and when the channel tube 15 extending from the proximal end of the insertion portion 2 is slightly shortened due to manufacturing errors or the like, the manufacturing errors or the like can be adjusted with the tube insertion hole 28d as long as a sufficient length of the tube insertion hole 28d is ensured to maintain the insertion state of the channel tube 15. Therefore, the length of the channel tube 15 can be easily managed, and the workability may be further improved.

Incidentally, since the endoscope 1 of the present embodiment is a disposable endoscope and does not require cleaning under high temperature and high pressure, as long as a treatment instrument is inserted into the channel tube 15, sealing the connection portion between the forceps pipe sleeve 28 and the channel tube 15 is not particularly necessary. Meanwhile, when the seal retention hole 28e configuring the inner periphery of the forceps pipe sleeve 28 and the outer periphery of the channel tube 15 are sealed by the O-ring 45 which is a sealing member, the airtightness and the liquid-tightness of the connection portion between the forceps pipe sleeve 28 and the channel tube 15 may be secured. When such a seal structure is adopted, the channel tube 15 may be utilized not only for insertion of a treatment instrument or the like but also as a channel for air feeding and water feeding. In this case, by providing the partition wall 46 facing the distal end of the forceps pipe sleeve 28 inside the first housing member 30, the O-ring 45 may be appropriately prevented from falling off from the forceps pipe sleeve 28 with a simple configuration, and the sealing performance can be maintained.

Alternatively, since the partition wall 46 and the guide wall 47 are integrally formed with the first housing member 30, an increase in the number of components may be appropriately suppressed and simplification of the structure can be realized.

Here, the guide wall 47 may contact with outer side portion of the bend of the channel tube 15, but the case is not limited to such that the guide wall 47 is provided in advance to contact with the outer side portion of the bend of the channel tube 15, and a gap may be provided between the guide wall 47 and the channel tube 15 to such an extent that the channel tube 15 does not come off from the forceps pipe sleeve 28, and the guide wall 47 may come into contact with the channel tube 15 when the channel tube 15 is pressed toward the outer side direction of the bend.

Here, in the above-described embodiment, an example of a configuration in which the guide wall 47 is integrally formed with the first housing member 30 has been described. However, for example, the guide wall 47 may be integrally formed with the second housing member 31.

Figure 5:
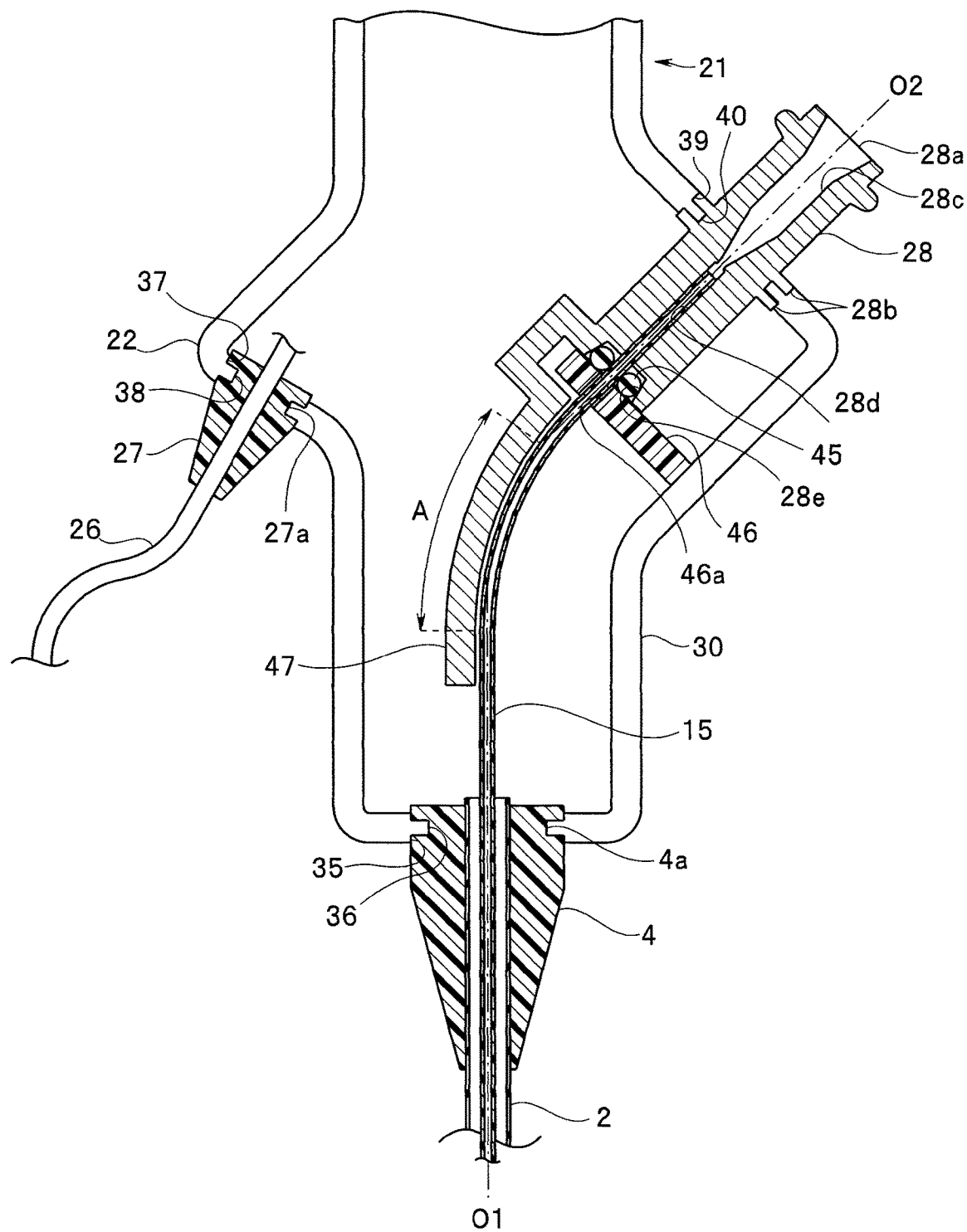
FIG. 5 is a cross-sectional view illustrating a main portion of an operation portion according to a first modification.

In addition, the guide wall 47 may be provided on a member supported by at least one of the first housing member 30 and second housing member 31. For example, as illustrated in FIG. 5, the guide wall 47 may be integrally formed with the forceps pipe sleeve 28 that is supported between the first housing member 30 and second housing member 31. Further, although not illustrated, the guide wall 47 may be provided on a stay or the like that reinforces the housing 20.

Figure 6:
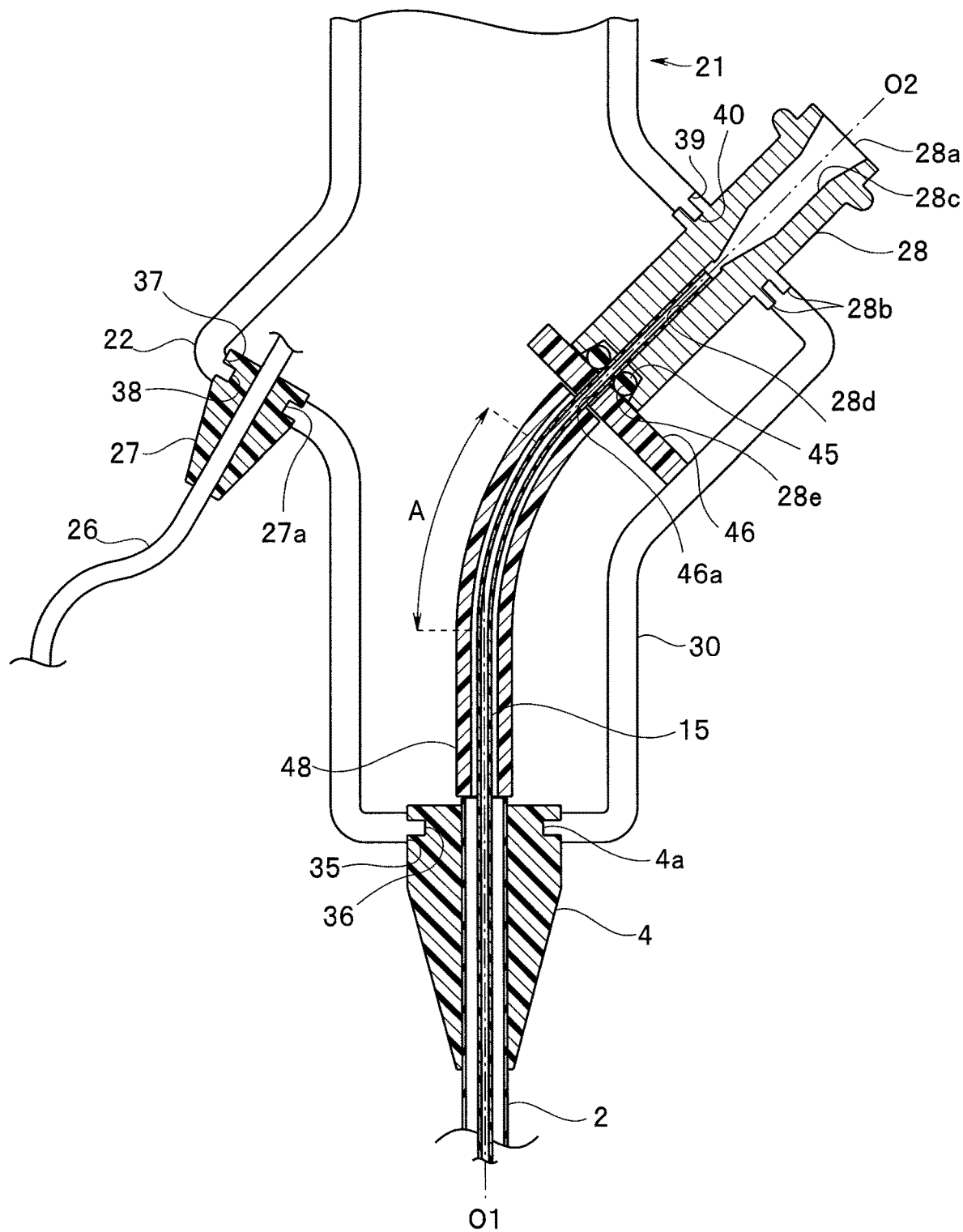
FIG. 6 is a cross-sectional view illustrating a main portion of an operation portion according to a second modification.
Figure 7:
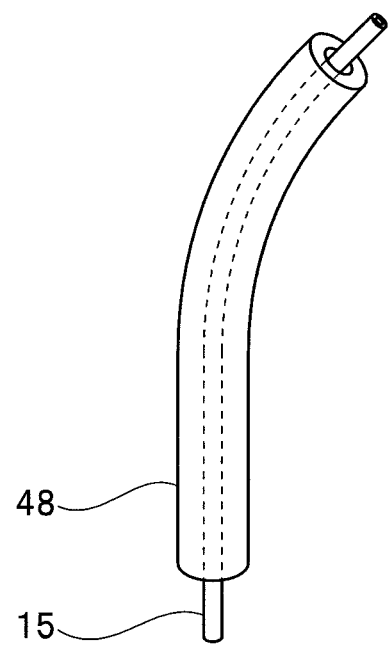
FIG. 7 is a perspective view illustrating a channel tube inserted into a guide tube according to the second modification.

Further, for example, as illustrated in FIGS. 6 and 7, instead of the guide wall 47, a bending tube 48 through which the channel tube 15 is inserted may configure the auxiliary member.

In this case, for example, as illustrated in FIG. 6, the bending tube 48 is formed in a bending shape similar to the bending shape in which the channel tube 15 is to be disposed inside the operation portion 3. In addition, the length of the bending tube 48 is desirable to be set to a length in which one end abuts on the proximal end of the insertion portion 2 or the proximal end of the bend preventing portion 4, and the other end abuts on the partition wall 46.

Figure 8:
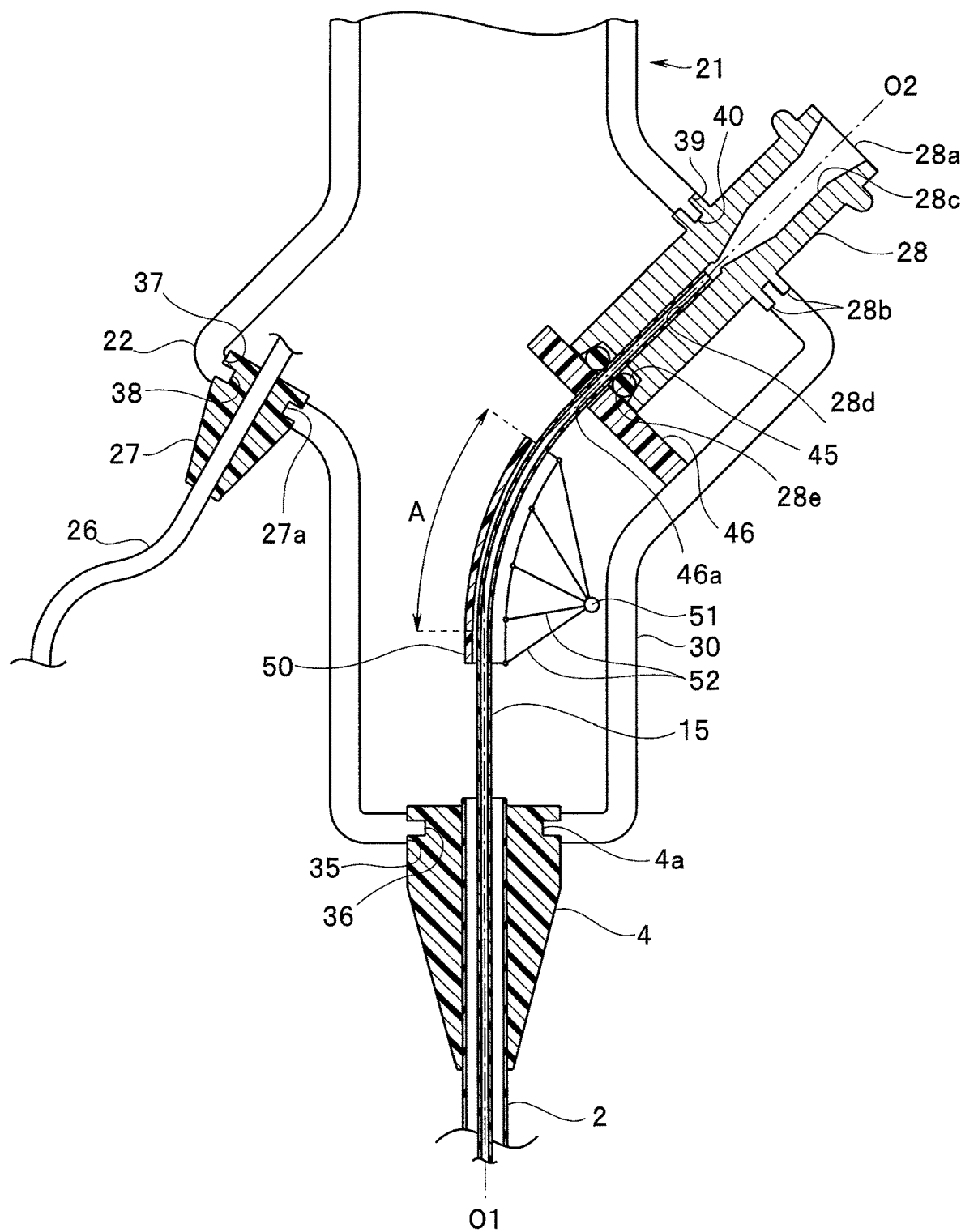
FIG. 8 is a cross-sectional view illustrating a main portion of an operation portion according to a third modification.
Figure 9:
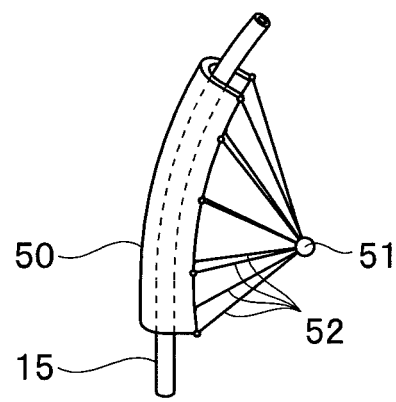
FIG. 9 is a perspective view illustrating a channel tube supported by a guide sheet according to the third modification.

Further, for example, as illustrated in FIGS. 8 and 9, instead of the guide wall 47, the auxiliary member may be configured by a sheet 50 provided in contact with the channel tube 15 and covering the channel tube 15.

In this case, for example, by providing a support pin 51 inside the first housing member 30 and connecting the sheet 50 and the support pin 51 by a plurality of wires 52, the sheet 50 may be disposed inside the operation portion 3 in a bent state along the bending shape of the channel tube 15.

It should be noted that the present invention is not limited to the embodiments described above, and various modifications and changes can be made without departing from the technical scope of the present invention.

What is claimed is:

1. An endoscope, comprising:
   an operation portion;
   a port tube provided in the operation portion, the port tube having a channel;
   a channel tube inserted into the port tube to communicate with the channel;
   a seal disposed between a distal end side of the port tube and the channel tube, and
   a partition surface for restricting movement of the seal and of the tube;

wherein the port tube having a first width in a direction intersecting with a longitudinal axis of the port tube, and the partition surface has a second width being larger than the first width in the direction.

2. The endoscope according to claim 1, wherein the partition surface protruding from an inner surface of the operation portion.

3. The endoscope according to claim 2, wherein the port tube has a recess at a distal end of the tube, the recess having a bottom surface; and when the seal is disposed between the port tube and the partition surface, an interval between the partition surface and the bottom surface is less than a thickness of the seal.

4. The endoscope according to claim 2, wherein the partition surface is integrally formed with the operation portion.

5. The endoscope according to claim 2, wherein the partition surface is a wall portion having:
a flat surface facing an end of the port tube; and
a U-shaped slit, and
the channel tube is inserted through the U-shaped slit.

6. The endoscope according to claim 2, wherein the seal is disposed between an inner periphery of the port tube and an outer periphery of the channel tube, and the seal is configured to restrict the channel tube from falling off from the port tube by a restoring force of the seal as compressed by the port tube and the partition surface.

7. The endoscope according to claim 6, wherein the seal comprises an O-ring.

8. The endoscope according to claim 7, wherein when the O-ring is compressed by the port tube and the partition surface, the O-ring water tightly secures the port tube to the channel tube.

9. The endoscope according to claim 1, further comprising:
an auxiliary member provided inside the operation portion and configured to contact with an outer surface of a curved portion of the channel tube.

10. The endoscope according to claim 9, wherein the auxiliary member is integrally formed with the operation portion.

11. The endoscope according to claim 9, wherein the auxiliary member is provided in contact with an outer side portion of the curved portion of the channel tube to restrict movement of the channel tube away from the port tube.

12. The endoscope according to claim 11, wherein the auxiliary member is a wall surface provided along the curved portion of the channel tube.

13. The endoscope according to claim 9, wherein the auxiliary member is an auxiliary tube covering the channel tube.

14. The endoscope according to claim 9, wherein the auxiliary member is more rigid than the channel tube.

15. The endoscope according to claim 9, wherein an angle formed by a central axis of the port tube and the auxiliary member is 45 degrees or less.

16. The endoscope according to claim 1, further comprising:
an operation body;
an auxiliary protrusion protruded from an inner surface of the operation body, the auxiliary protrusion including:
a first surface configured to contact with an outer surface of the channel tube; and
a second surface opposite to the first surface, the second surface facing a part of the inner surface and spaced from the part of the inner surface.

17. The endoscope according to claim 1, further comprising:
an operation body; and
an auxiliary protrusion protruded from an inner surface of the operation body in a first direction, the auxiliary protrusion is configured to restrict a movement of the channel tube in a second direction intersecting with the first direction.

18. The endoscope according to claim 1, further comprising:
an operation body; and
an auxiliary protrusion protruded from an inner surface of the operation body;
wherein the channel comprises:
a first portion provided in the port tube, the first portion extending along a first axis;
a second portion provided in an insertion portion, the second portion extending along a second axis; and
a curved portion located between the first portion and the second portion, the curved portion contacting the auxiliary protrusion, the port tube provided closer to the curved portion than the second axis.

19. The endoscope according to claim 1, further comprising:
an operation body; and
an auxiliary protrusion protruded from an inner surface of the operation body;
wherein the channel tube comprises a portion provided in an insertion portion, the portion extending along an axis, and
a part of the auxiliary protrusion is provided on the axis.

20. An endoscope, comprising:
an operation portion;
a port tube provided in the operation portion, the port tube having a channel;
a channel tube inserted into the port tube to communicate with the channel;
a seal disposed between a distal end side of the port tube and the channel tube, and
a partition surface protruding from an inner surface of the operation portion to restrict movement of the seal and of the tube;
wherein the partition surface is a wall portion having:
a flat surface facing an end of the port tube; and
a U-shaped slit, and
the channel tube is inserted through the U-shaped slit.

* * * * *